United States Patent [19]

Buonomo et al.

[11] Patent Number: 4,746,643
[45] Date of Patent: May 24, 1988

[54] METHOD FOR THE PREPARATION OF A CATALYST FOR THE DEHYDROGENATION OF $C_3$-$C_5$ PARAFFINS

[75] Inventors: Franco Buonomo, San Donato Milanese; Rodolfo Jezzi, San Vito Chietino; Bruno Notari, San Donato Milanese, all of Italy; Gheorghiy R. Kotelnikov, Yaroslavl, U.S.S.R.; Konstantinovic R. Michailov, Yaroslavl, U.S.S.R.; Victor A. Patanov, Yaroslavl, U.S.S.R.

[73] Assignees: Snamprogetti S.p.A., Milan, Italy; Niimsk, Yaroslavl, U.S.S.R.

[21] Appl. No.: 874,579

[22] Filed: Jun. 16, 1986

[30] Foreign Application Priority Data

Jun. 17, 1985 [IT]   Italy ................................ 21180 A/85

[51] Int. Cl.$^4$ .......................... B01J 23/04; B01J 23/26
[52] U.S. Cl. ....................................... 502/243; 502/256
[58] Field of Search ............................... 502/243, 256

[56] References Cited

U.S. PATENT DOCUMENTS 2,991,255  7/1961  Malley et al. ...................... 502/320
3,446,865  5/1969  Roth et al. ...................... 502/183 X

FOREIGN PATENT DOCUMENTS 1185246  3/1970  United Kingdom ................ 502/243
 789151 12/1980  U.S.S.R. ............................. 502/243

Primary Examiner—Patrick P. Garvin
Attorney, Agent, or Firm—Hedman, Gibson, Costigan & Hoare

[57] ABSTRACT

The invention relates to a method for the preparation of a catalyst for the dehydrogenation of $C_3$-$C_5$ paraffins consisting in impregnating calcined aluminum oxide with a solution of chromium and potassium compounds, in drying and then impregnating the product obtained with a solution of a compound of silicon, the catalyst obtained being finally dried and calcined.

13 Claims, No Drawings

METHOD FOR THE PREPARATION OF A CATALYST FOR THE DEHYDROGENATION OF C₃-C₅ PARAFFINS

The present invention relates to a method for the preparation of a catalyst for the dehydrogenation of $C_3$-$C_5$ paraffins.

In the art, methods are known for the preparation of catalysts for the dehydrogenation of paraffins, on the basis of aluminum, chromium and potassium, and in which the support is a porous support containing $Al_2O_3$ and $SiO_2$ (U.S. Pat. No. 3,446,865 and U.S.S.R. Pat. No. 202,791).

The disadvantages of the methods known from the prior art can be identified as relatively poor stability, activity and mechanical strength of the catalysts produced.

A further method is the method for the preparation of a catalyst on the basis of aluminum and chromium for the dehydrogenation of hydrocarbons consisting of impregnating aluminum oxide first with solutions of compounds of silicon and potassium, and then with a solution of a chromium compound, with further drying and calcination of the catalyst obtained (U.S. Pat. No. 2,991,255). The drawbacks of this latter method are again poor activity, mechanical strength and stability of the catalyst.

It has been surprisingly found that it is possible to obtain a high-activity catalyst, having high mechanical strength and stability, by operating according to a particular sequence of steps.

The object of the present invention is a method for the preparation of a catalyst for the dehydrogenation of $C_3$-$C_5$ paraffins (paraffins containing a number of from 3 to 5 carbon atoms), on the basis of aluminum, chromium, potassium and silicon, according to which aluminum oxide ($Al_2O_3$) having the form of microspheres (20-150 μm) is calcined a first time at temperatures comprised within the range of from 500° to 700° C., preferably around 600° C., is then calcined a second time at temperatures higher than 1000° C., preferably around 1100° C., for many hours, the calcined product is then impregnated with a solution containing chromium and potassium compounds, or with separated solutions of said chromium and potassium compounds, the product is then dried and impregnated with a solution of a compound of silicon, and is finally dried and calcined at temperatures of up to 700° C.

As silicon compounds, the compounds of silicon which decompose at 0°–500° C. by oxidation or hydrolysis can be used.

Examples of such compounds are: $Si(OC_2H_5)_4$, $C_2H_5$-$SiCl_3$, $C_6H_5$-$Si(C_2H_5)Cl$ and other compounds having the general formula:

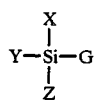

wherein X, Y, G and Z can be composed by (—R), (—Cl), (—Br), (—SiH), (—COOR), (—SiH$_r$Cl$_m$), wherein R is an alkyl, cycloalkyl, aromatic or alkylcycloalkyl group having from 1 to 30 carbon atoms; r and s have values comprised between 1 and 2, their sum being 3.

As chromium compounds, compounds able to yield $Cr_2O_3$ by calcination, in particular $CrO_3$, are used; and as potassium compounds, salts of potassium which can be decomposed to yield $K_2O$ by calcination are used, such as, e.g., $K_2CO_3$.

The catalyst obtained by the method according to the present invention has the following end elemental composition, as expressed as oxides:

$SiO_2$ 0.5%–3% by weight, preferably 1%–2% by weight;

$K_2O$ 0.5%–3% by weight, preferably 1%–2% by weight;

$Cr_2O_3$ 10%–25% by weight, preferably 12%–20% by weight; the balance being $Al_2O_3$.

By using the method of the invention, the active catalyst portion comprising chromium, potassium and aluminum under conditions of high dispersion and homogeneously distributed, after being treated with the compound of silicon, is fixed in this position by a lattice of oligomeric $SiO_2$. Such fixing prevents the active phase from crystallizing during the calcination and the subsequent use of the catalyst, and ensures a high activity, mechanical strength and stability.

The invention is illustrated in a non-limitative way by the following Examples:

EXAMPLE 1

A microspheroidal (20-150 μm) γ-$Al_2O_3$ is prepared by spray-drying of a solution of aluminum salts, or of a suspension of aluminum oxide hydrate obtained by precipitation from a solution of an aluminum salt.

After drying and calcination at 600° C. for 1 hour, γ-$Al_2O_3$ is the form of microspheres is obtained, with a surface area of 280 m²/g and a volume of pores, with their radii being comprised within the range of from 0 to 70 Å, of about 0.61 cm³/g.

The product is transferred into a high-temperature oven and is treated 24 hours at 1100° C. with air. During such a treatment, $Al_2O_3$ is transformed into delta, beta and alpha phases, reaching a specific surface area of 65 m²/g and a porosity of 0.22 cm³/g, with an average pore diameter of 20 μm.

The aluminum oxide so obtained is impregnated with an aqueous solution of $Cr_2O_3$ and $K_2CO_3$, by operating according to the following procedure:

Twenty-five g is prepared of a solution containing 15.8 g of $CrO_3$ and 2.22 g of $K_2CO_3$; the solution is heated up to 50° C. and is slowly added to 100 g of aluminum oxide. After the end of the addition of the solution, the perfectly and homogeneously impregnated catalyst is heated inside a fluidized-bed reactor up to 250° C. under a $N_2$ stream, to remove impregnating liquors, it is then cooled to room temperature, and aluminum oxide so obtained is treated with $Si(OC_2H_5)_4$ according to the following procedure:

From the bottom of the reactor, through a porous distributor, $N_2$ is fed into the reaction vessel at such a flow rate as to have inside the reactor a linear speed of gases of about 2 cm/second, which allows the catalytic bed to be fluidized. From the reactor top, while the cataltyic bed being kept at room temperature, an alcoholic solution of $Si(OC_2H_5)_4$, obtained by dissolving 7 g of ethyl silicate in 60 g of ethyl alcohol is introduced dropwise.

At the end of the delivery of the solution, while continuing feeding $N_2$ from below, heating of the bed is started, until it reaches the temperature of 550° C., at the heating rate of 5°/minute. At this temperature the feed of $N_2$ is discontinued, air is fed, and heating of the catalyst is continued until the temperature of 700° C. is reached, at which temperature the catalyst is kept 1 hour.

At the end, a catalyst having the following chemical composition is obtained:

$Al_2O_3$: 84.4%; $SiO_2$: 2%; $K_2O$: 1.4%; $Cr_2O_3$: 12.2%

It has the following physical-chemical characteristics: surface area, porosity, volumetric density respectively of 55–65 m$^2$/g, 0.28 cm$^3$/g, 1.3 gcm$^3$.

EXAMPLE 2

The catalyst is prepared as in Example 1, but as the silicon compound, ethyl-phenyl-dichlorosilane $C_6H_5.Si(C_2H_5).Cl_2$ is taken (in the amount necessary to the purpose of having the same composition as of Example 1).

EXAMPLE 3

The catalyst is prepared as in Example 1, but as the silicon compound, ethyl-triethoxysilane $(C_2H_5O)_3.Si(C_2H_5)$ is taken (in the amount necessary to the purpose of having the same composition as of Example 1).

EXAMPLE 4

The catalyst is prepared as in Example 1, but as the silicon compound, tetrabenzylsilane $(C_6H_5CH_2)_4.Si$ is taken (in the amount necessary to the purpose of having the same composition as of Example 1).

EXAMPLE 5

The catalyst is prepared as in Example 1, but a commercial aluminum oxide (HARSHAW 13912) is used (in the amount necessary to the purpose of having the same composition as of Example 1).

EXAMPLE 6

(Comparative Example)

Microspheroidal $Al_2O_3$ is prepared by following the procedure as of Example 1, but to the suspension of aluminum oxide hydrate (100 g of $Al_2O_3$), before feeding it to the spray-drier, commercial colloidal $SiO_2$ (DU PONT) is added in the amount of 5 g. The $Al_2O_3/SiO_2$ mixture is then submitted to the heat treatment and is impregnated with 25 g of solution containing 15.8 g of $CrO_3$ and 2.2 g of $K_2CO_3$, by following the same method as disclosed in Example 1.

The catalysts obtained are tested in the processes of dehydrogenation of propane, isobutane, n.butane and isopentane, carried out at the temperature of 580° C., under atmospheric pressure and at space speed (by volume) of 400 h$^{-1}$ in a fluid-bed laboratory-scale reactor.

The mechanical strength of the catalysts is evaluated according to the "Standard Oil" methodology, as described in Industrial Engineering Chemistry Vo. 41, No. 6, pages 1200–1206. The results are reported in Table 1. The stability of catalysts is evaluated on the basis of the changes in observed parameters after the calcination in an air stream at 800° C. for 600 hours (Table 2).

From the data shown, it can be observed that the use of silicon compounds in the end step of the preparation route allows considerable improving the catalytic characteristics, the stability and the mechanical properties of the catalyst on the basis of aluminum, chromium and potassium.

TABLE 1

| Catalyst/ Example No. | Friction Index | Testing of Catalysts | | | | | | | |
|---|---|---|---|---|---|---|---|---|---|
| | | Isobutane Dehydrogenation | | N—butane Dehydrogenation | | Iso-pentane Dehydrogenation | | Propane Dehydrogenation | |
| | | Conversion | Selectivity | Conversion | Selectivity | Conversion | Selectivity | Conversion | Selectivity |
| 1 | 3.6 | 53.3 | 88.6 | 51.4 | 79.5 | 48.8 | 67.1 | 45.1 | 82.2 |
| 2 | 4.2 | 53.0 | 88.8 | 51.1 | 79.3 | 48.7 | 67.0 | 44.0 | 82.5 |
| 3 | 4.0 | 53.6 | 88.1 | 51.3 | 79.1 | 48.5 | 67.2 | 45.1 | 81.1 |
| 4 | 5.0 | 53.5 | 88.2 | 51.4 | 79.3 | 48.7 | 67.0 | 46.1 | 81.5 |
| 5 | 4.6 | 56.0 | 83.0 | 52.3 | 76.5 | 49.1 | 64.3 | 47.1 | 78.1 |
| 6 (Comparative Example) | 11.8 | 45.1 | 87.2 | 45.1 | 76.0 | 42.9 | 66.2 | 40.1 | 79.0 |

Friction Index = % by weight of fine products formed according to Industrial Engineering Chemistry, Vol. 41, No. 6, pages 1200–1206

TABLE 2

| Catalyst from Various Examples | Tests on Catalysts after a 600-hrs Calcination at 800° C. | | | | | |
|---|---|---|---|---|---|---|
| | Specific Surface Area (m2/g) | | Isobutane Dehydrogenation | | N—butane Dehydrogenation | |
| | Initial | After Calcination | Conversion | Selectivity | Conversion | Selectivity |
| 1 | 54 | 51 | 52.1 (−1.2) | 89.1 | 50.6 (−0.8) | 80 |
| 2 | 53 | 51 | 52.0 (−1) | 89.3 | 50.1 (−1) | 80.1 |
| 3 | 52 | 51 | 52.8 (−0.8) | 88.6 | 50.4 (−0.9) | 79.8 |
| 4 | 51 | 50 | 52.3 (−1.2) | 88.9 | 50.3 (−1.1) | 79.6 |
| 5 | 65 | 50 | 52 (−4) | 84 | 49.3 (−3) | 76.8 |
| 6 (Comparative Example) | 65 | 40 | 40 (−5.6) | 84 | 40.1 (−5) | 76 |

We claim:

1. A method for the preparation of a catalyst for the dehydrogenation of $C_3$-$C_5$ paraffins, on the basis of aluminum, chromium, potassium and silicon, comprising (1) calcining aluminum oxide having the form of microspheres a first time at temperatures of from 500° to 700° C., (2) calcining the aluminum oxide a second time at temperatures higher than 1000° C., (3) impregnating the calcined product with a solution containing chromium and potassium compounds, or with separate solutions of said chromium and potassium compounds, (4) drying the product and then impregnating it with a solution of a silicon compound, and (5) drying and calcining the product at temperatures of up to 700° C.

2. The method according to claim 1, characterized in that said aluminum oxide is in the form of microspheres having a diameter comprised within the range of from 20 to 150 μm.

3. The method according to claim 1, characterized in that the first calcination of aluminum oxide is carried out at a temperature around 600° C.

4. The method according to claim 1, characterized in that the second calcination of aluminum oxide is carried out at a temperature around 1100° C.

5. The method according to claim 1, characterized in that as the silicon compounds, compounds are used which undergo decomposition at 0° C.–500° C. by oxydation or hydrolysis.

6. The method according to claim 1, characterized in that the silicon compounds have the following general formula:

wherein X, Y, G and Z are (—R), (—Cl), (—Br), (—SiH), (—COOR) or (—SiH$_r$Cl$_m$), wherein R is an alkyl, cycloalkyl, aromatic or alkylcycloalkyl group having from 1 to 30 carbon atoms; r and m having values comprised between 1 and 2, their sum being 3.

7. The method according to claim 5, characterized in that the silicon compounds are selected from the group consisting of Si(OC$_2$H$_5$)$_4$, C$_2$H$_5$-SiCl$_3$ and C$_6$H$_5$-Si(C$_2$H$_5$)Cl$_2$.

8. The method according to claim 1, characterized in that the compounds of chromium are compounds able to yield Cr$_2$O$_3$ by calcination.

9. The method according to claim 1, characterized in that the compounds of potassium are salts which can be decomposed to yield K$_2$O by calcination.

10. The method according to claim 9, characterized in that the compound of potassium is K$_2$CO$_3$.

11. The method according to claim 8, wherein the chromium compound is CrO$_3$.

12. The method according to claim 1, wherein the second calcining of the aluminum oxide is carried out until said aluminum oxide is transformed into delta, beta and alpha phases.

13. The method of claim 1, wherein the second calcining of the aluminum oxide is carried out for up to 24 hours.

* * * * *